United States Patent
Sello et al.

(10) Patent No.: US 9,057,698 B2
(45) Date of Patent: Jun. 16, 2015

(54) METHODS OF CHEMOSELECTIVE DERIVATION OF MULTIPLE CLASSES OF METABOLITES

(75) Inventors: Jason K. Sello, Providence, RI (US); Kyle A. Totaro, East Providence, RI (US); Babajide O. Okandeji, Providence, RI (US)

(73) Assignee: Brown University, Providence, RI (US)

( * ) Notice: Subject to any disclaimer, the term of this patent is extended or adjusted under 35 U.S.C. 154(b) by 141 days.

(21) Appl. No.: 13/586,193

(22) Filed: Aug. 15, 2012

(65) Prior Publication Data

US 2013/0071940 A1 Mar. 21, 2013

Related U.S. Application Data

(60) Provisional application No. 61/625,339, filed on Apr. 17, 2012, provisional application No. 61/605,984, filed on Mar. 2, 2012, provisional application No. 61/524,082, filed on Aug. 16, 2011.

(51) Int. Cl.
*G01N 27/62* (2006.01)
*G01N 24/08* (2006.01)
*G01N 27/00* (2006.01)
*G01N 24/00* (2006.01)
*G01N 33/50* (2006.01)
*G01R 33/465* (2006.01)

(52) U.S. Cl.
CPC ............... *G01N 27/62* (2013.01); *G01N 24/08* (2013.01); *Y10T 436/17* (2015.01); *Y10T 436/147777* (2015.01); *Y10T 436/145555* (2015.01); *Y10T 436/172307* (2015.01); *G01R 33/465* (2013.01); *G01N 33/50* (2013.01)

(58) Field of Classification Search
CPC ....... G01N 24/08; G01N 27/62; G01N 27/00; Y10T 436/00; Y10T 436/17; Y10T 436/172307
USPC .............................. 436/98, 106, 96
See application file for complete search history.

(56) References Cited

PUBLICATIONS

Okandeji, B.O., "Multicomponent Reactions: Catalysis, Mechanisms and Applications." A Dissertation submitted in partial fulfillment of the requirements for the Degree of Doctor of Philosophy in the Department of Chemistry at Brown University, Providence, Rhode Island (May 2011).

Okandeji, B.O., "Multicomponent Reactions: Catalysis, Mechanisms and Applications." A Dissertation submitted in partial fulfillment of the requirements for the Degree of Doctor of Philosophy in the Department of Chemistry at Brown University, Providence, Rhode Island (Public Availability Date: Jan. 17, 2012).

*Primary Examiner* — Christine T Mui
(74) *Attorney, Agent, or Firm* — Hamilton, Brook, Smith & Reynolds, P.C.

(57) ABSTRACT

Chemoselective derivatization of biological amines, carboxylic acids, aldehydes or ketones are employed in methods to detect a plurality of components, or members of a component, such as metabolites, that vary in molecular structure. The methods of the invention can be employed in aqueous and nonaqueous conditions.

12 Claims, 6 Drawing Sheets
(3 of 6 Drawing Sheet(s) Filed in Color)

METHODS OF CHEMOSELECTIVE DERIVATION OF MULTIPLE CLASSES OF METABOLITES

RELATED APPLICATION(S)

This application claims the benefit of U.S. Provisional Application Nos. 61/625,339, filed on Apr. 17, 2012, 61/605,984, filed on Mar. 2, 2012, and 61/524,082, filed on Aug. 16, 2011. The entire teachings of the above applications are incorporated herein by reference.

GOVERNMENT SUPPORT

This invention was made with government support under MCB1053319 awarded by National Science Foundation. The government has certain rights in the invention.

BACKGROUND OF THE INVENTION

The relative concentration, stability and structural diversity of metabolites in biological samples present challenges in systems biology and in diagnostic medicine when the goal is to analyze several (e.g., dozens or hundreds) of metabolites that can vary in chemical structure (e.g., aminos, ketones, carboxylic acids). Typically, a specific reagent is used to derivatize one structural class of metabolites for each analysis. This "one reagent-one functional group" method can be technically cumbersome when analyzing metabolites of varying structures in a biological sample. Thus, there is a need to develop new methods to analyze metabolites of varying chemical structure in a sample.

SUMMARY OF THE INVENTION

The invention is generally directed to methods of identifying molecules of varying chemical structure (e.g., amines, aldehydes, carboxylic acid) in a biological sample. In particular, the invention is directed to a method of identifying components in a biological sample, that includes the steps of combining at least a portion of a biological sample, the biological sample including at least one component that is, or includes (i) an amino acid or an amine, (ii) an aldehyde or a ketone, or (iii) a carboxylic acid or an alcohol, with an isocyanide and Ugi reactants that consists essentially of two of (i),(ii) and (iii) apart from the component, thereby derivatizing at least a portion of that component and identifying the derivatized component of the biological sample.

In one embodiment, wherein the component is a first component, and wherein the biological sample includes a second component that is, or includes, i) an amino acid or amine, ii) an aldehyde or a ketone, or iii) a carboxylic acid or an alcohol, that is not any of i), ii) or iii) of the first component, the method further includes the steps of combining at least a portion of the remainder of the biological sample with an isocyanide and Ugi reactants that consist essentially of two of i), ii) and iii) apart from the second component, thereby dirivatizing at least a portion of the second component, and identifying the derivatized second component.

In another embodiment, the isocyanide is labeled, isotopic or ionic. In still another embodiment, the component is selected from the group consisting of proteins, polyamines, fatty acids, neurotransmitters, hormones, α-amino acids, intermediates in central metabolism, antibiotics, carbohydrates, co-factors and co-enzymes.

In one, specific embodiment the reactants are in molar excess to the component of the biological sample.

In still another embodiment, the biological sample includes a plurality of chemically distinct members of the component, wherein the members share a common functional group of, i) an amino acid or an amine, ii) an aldehyde or ketone, or iii) a carboxylic acid or an alcohol.

In still another embodiment, the method further includes the step of identifying derivatized members of the component by separating at least a portion of the derivatized members from each other.

In another embodiment, the derivatized members of the component are separated from each other by liquid chromatography. In yet another embodiment, the derivatized members of the component are identified, at least in part, by mass spectroscopy or nuclear resonance spectroscopy.

The invention has the advantage, for example, of identifying a class of molecules of biological samples, such as metabolites or various proteinogenic α-amino acids, by a single reaction. In addition, a single biological sample that includes a plurality of components can be separated and tested for different components that include functional groups that participate in Ugi four-component or Ugi-four-component-five center reactions by using a different set of Ugi reactants on each portion of the biological sample.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
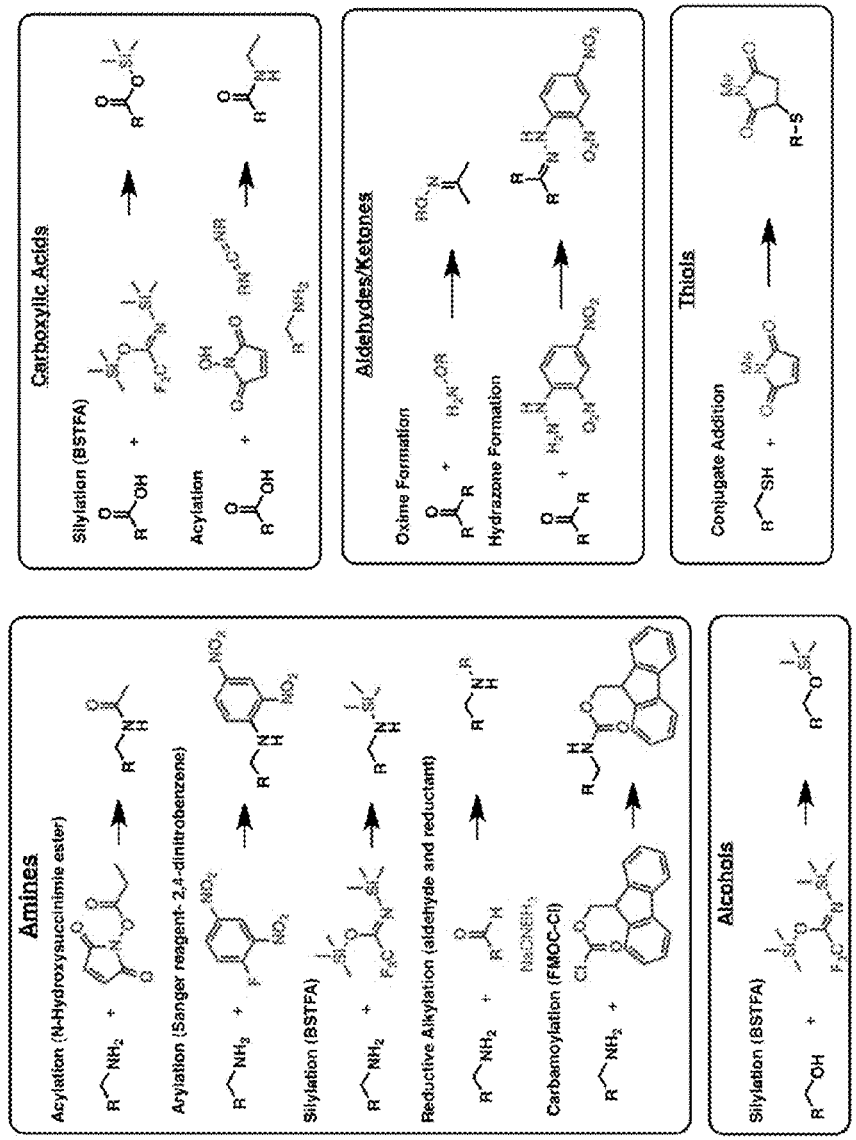
FIG. 1 depicts prior art derivation reactions and reagents (depicted in red) employed in biological chemistry.

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

In an embodiment, the invention is directed to a method of identifying components in a biological sample, that includes the steps of combining at least a portion of a biological sample, the biological sample including at least one component that is, or includes (i) an amino acid or an amine, (ii) an aldehyde or a ketone, or (iii) a carboxylic acid or an alcohol, with an isocyanide and Ugi reactants that consists essentially of two of (i),(ii) and (iii) apart from the component, thereby derivatizing at least a portion of that component and identifying the derivatized component of the biological sample.

"Biological sample," as that term is employed herein, means a sample that is drawn from or excreted by a mammal, such as a human being. In one embodiment, the biological sample can be a fluid sample that has been physically or chemically treated before being employed in the method of the invention, so long as the biological sample includes more than one component.

A "component," as that term is employed herein, means a chemical compound that can be found in a biological sample, and that is, or includes: i) and amino acid or an amine; ii) an aldehyde or a ketone; or iii) a carboxylic acid or an alcohol. The biological sample employed in the methods of the invention can include a plurality of distinct members of a class of component, said members having distinct chemical formulas, such as distinct amino acids, including, for example, a plurality of proteinogenic α-amino acids. Alternatively, the class of component can be a class of chemical compounds that includes an amine, an aldehyde, a ketone, a carboxylic acid or an alcohol. Optionally, or alternatively, the biological sample can include two, three, four, five, six, seven, eight, nine, ten or more different components.

In the methods of the invention, when the component is a first component, and the biological sample includes a second component that is, or includes i) an amino acid or an amine, ii) an aldehyde or a ketone, or iii) a carboxylic acid or an alcohol, that is not any of i), ii) or iii) of the first component, the methods of the invention can further include combining at least a portion of the remainder of the biological sample with an isocyanide and Ugi reactants that consists essentially of two of i) an amino acid or an amine, ii) an aldehyde or a ketone, or iii) a carboxylic acid or an alcohol, to derivatize at least a portion of the second component and identify the derivatized second component. If the biological sample includes a plurality of components having functional groups that are derivatized by different Ugi four-component or Ugi-four-component-five center reactions, then the sample can be split into different parts with different Ugi four-component or Ugi-four-component-five-center reactions being conducted in each sample.

The isocyanide employed in the methods of the invention can be labeled, isotopic or ionic. A labeled isocyanide can be a chromophoric labeled isocyanide that is UV detectable. An isotopic isocyanide can be a radiolabeled isocyanide (e.g., tritium) and detectable by NMR or radioactive decay, for example. The labeled isocyanide can be labeled by ionization, such as cationic ionization or anionic ionization and detectable by mass spectrometry. The labeled isocyanide can be a fluorine-tagged isocyanide. Exemplary techniques for labeling isocyanide are described in Brittain, S., et al., *Nature Biotechnology* 23:463-468 (2005) and Portal, C., et al., *Org Biomol Chem* 5:587-592 (2007).

The component in the biological sample can be at least one member selected from the group consisting of proteins, polyamines, fatty acids, neurotransmitters, hormones, α-amino acids, intermediates in central metabolism, antibiotics, carbohydrates, co-factors and co-enzymes. For example, phenylalanine, phenothylamine, phenylpyruvic acid, phenyllactic acid and phenylacetic acid can be detected in phenylketonuria and sarcosene can be detected in prostate cancer.

The reactants employed in the methods of the invention can be in molar excess to the component of the biological sample, for example, molar ratios of at least 10:1.

The methods of the invention can further include the separating at least a portion of the derivatized members if a class of components from each other. Exemplary techniques to separate derivatized members of a class of a component from each other, includes liquid chromatography or fluorous chromatography.

The derivatized components or members of a class of a component can be identified, at least in part, by at least one member selected from the group consisting of mass spectroscopy, nuclear resonance spectroscopy, UV detection, or infrared spectroscopy.

Generally, low molecular weight metabolites and proteins are chemically modified during sample preparation to facilitate detection and separation in the sample. The modifications are typically based on the selective reaction of reagents with functional groups (i.e., aminos, carbohydrates) of biomolecules. For example, reactions of fluorodinitrobenzene (Sanger's reagent) and phenyl isothiocyanate (reagent in the Edman degradation) with the α-amino termini of peptides and proteins were used to facilitate protein sequencing and structural determination. Likewise, the carboxamate-yielding reaction of hydroxylamine with the carbonyl moieties of acetyl phosphate, acetyl-coenzyme A and aminoacyl-tRNAs were used to measure the activated esters in central metabolism. The covalent attachment of affinity labels and fluorescent tags to biomolecules has been used in protein biochemistry for the selective separations of proteins of interest. With few exceptions like the Staudinger ligation and the Click reaction, most chemical reactions and reagents in modern bioanalytical chemistry are those that have been used for the last half-century. Unfortunately, these chemistries are often low-yielding, prohibitively expensive and/or incompatible with some classes of biomolecules. Bioanalytical chemistry would benefit tremendously from the development of novel methods to detect biomolecules.

The Ugi four-component reaction of the invention can be used to selectively derivatize metabolites of a biological sample with either amine, carboxylic acid, aldehyde, or ketone moieties under a single set of reaction conditions. The reaction is compatible with aqueous conditions in which metabolites originate and it yields stable products that can be separated and ionized in LC-MS analysis. The inclusion of a specially designed UV-active isocyanide substrate in the Ugi reaction ensures that all the reaction products have a chromophore and thus can be easily detected. This derivatization of structurally and functionally diverse metabolites (e.g., neurotransmitters, hormones, and co-factors) for the analysis of biological samples.

"Biological sample," as that term is employed herein, means a fluid sample that is drawn or excreted by a mammal, such as a human being. In one embodiment, the biological sample can be a fluid sample that has been physically or chemically treated before being employed in the method of the invention, so long as the biological sample includes more than one component. A "component," as that term is employed herein, means a chemical compound that can be found in a biological sample, and that is, or includes: i) and amino acid or an amine; ii) an aldehyde or a ketone; or iii) a carboxylic acid or an alcohol. "Members of a class of a component," as defined herein, mean chemical compounds, such as proteinogenic α-amino acids, that share a common functional group that is a reactant in a Ugi four-component or Ugi four-component-five-center reaction.

Current-day analyses of organismal physiology (i.e., systems biology) and disease diagnosis have necessitated the identification, characterization and/or measurement of dozens or hundreds of metabolites in a biological sample. The general term for these types of analyses is called metabolomics. Although non-destructive methods, like NMR, have been applied, often metabolomic analyses involve the direct isolation of metabolites and determination of their masses. With some exceptions, these analyses are typically facilitated by derivatization.

Chemical derivatization has been useful in both GC-MS and LC-MS-based metabolomics as a means to impart metabolites with physicochemical properties that facilitate analysis. A limited subset of reactions has been used in the derivation of biomolecules for more than a decade (FIG. 1). Chemoselectivity in the derivitizations is achieved by the use of reagents with defined reactivity. For example, metabolites with amines have been derivatized with electrophilic reagents including 2,4-fluorodinitrobenzene, isothiocyanates, isocyanates, and N-hydroxysuccinimide esters. Oxime, hydrazone and imine-forming reactions have been utilized in the derivatization of aldehydes and ketones. Derivatization of carboxylic acids can be performed directly via reagent-based silylation or methylation, or indirectly via carbodiimide-promoted esterification. Although these "one reagent-one functional group" methods were designed for characterization of one or a small number of metabolites of interest, many groups have attempted to adapt the reagents for holistic studies of metabolism.

Metabolite Enrichment by Tagging and Proteolytic Release (METPR) exploits classical derivatization reagents by employing a solid supports functionalized with specific derivatization reagents for the selective capture of metabolites from complex biological samples. The captured metabolites are released for analysis by the action of a protease that cleaves the linker coupling the metabolites to the support. While this method has advantages with respect to simplifying the analytes, it is still a "one reagent-one functional group method" that requires a unique reagent and set of reaction conditions for each derivitzation.

Figure 2:
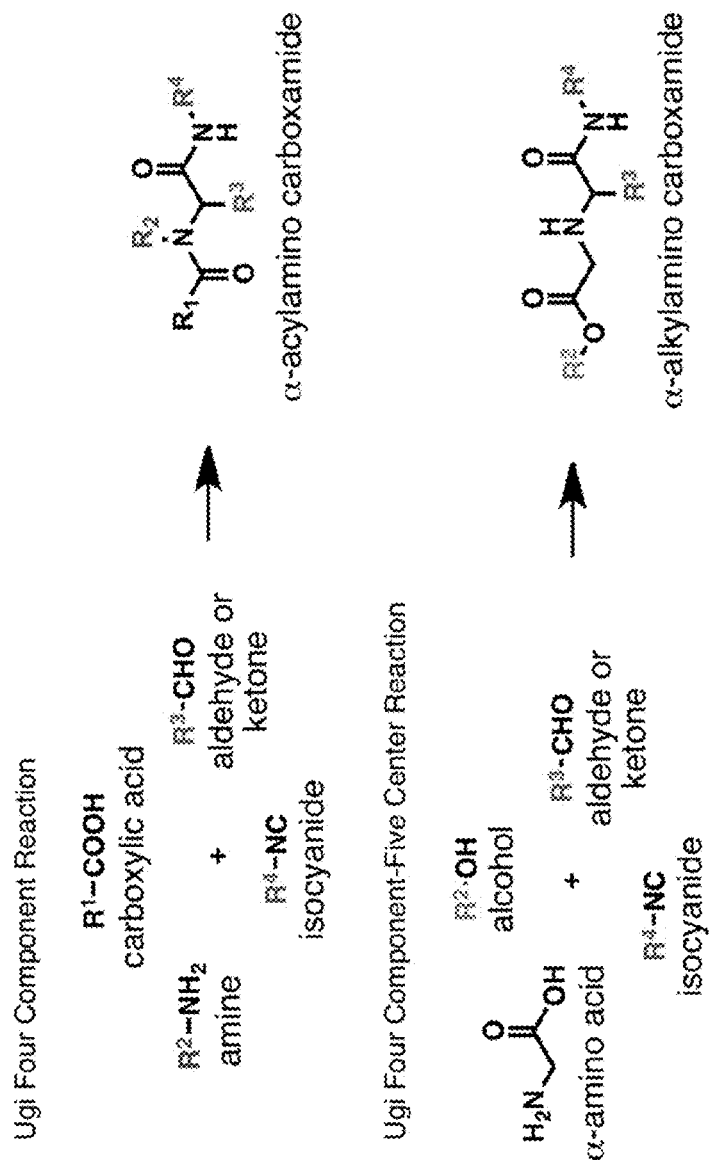
FIG. 2 depicts a prior art Ugi four-component and Ugi-four-component-five center reactions.

The inherent limitations of the classical reagents and the expanding demands of modern day metabolomics warrant the development of new methods for metabolite derivatization. New methods may include, for example; (1) operational simplicity, (2) chemoselectivity, (3) tolerance of aqueous conditions, and (4) be capable of providing stable and separable products that can be easily characterized with existing analytical instrumentation. As described herein, many of these criteria are met by using the Ugi 4-component reaction (U-4CR) for derivatization. In this multicomponent reaction (Scheme 1), an amine, an aldehyde or a ketone, a carboxylic acid, and an isocyanide react spontaneously to yield a stable peptide-like product (α-acylamino carboxamide) (FIG. 2). In the Ugi four-component-five-center reaction, an α-amino acid, aldehyde or ketone, and an isocyanide react spontaneously to yield a stable peptide-like product (α-alkylamino carboxamide). This reaction is generally high yielding and has a broad substrate scope and most metabolites have one or more functional groups that can participate in the reaction. The U-4CR is compatible with water and solvents typically used for metabolite extractions (i.e., acetonitrile, chloroform and methanol) and products of the reaction are readily analyzed by mass spectrometry. Chemoselectivity can be achieved by adding three additional reactants in molar excess relative to the analyte of interest (e.g., at least 10:1).

Scheme 1. The Ugi four-Component Reaction.

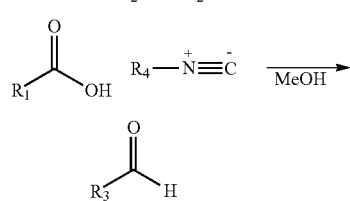

-continued

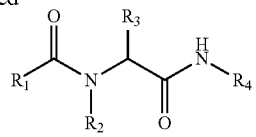

Figure 3:
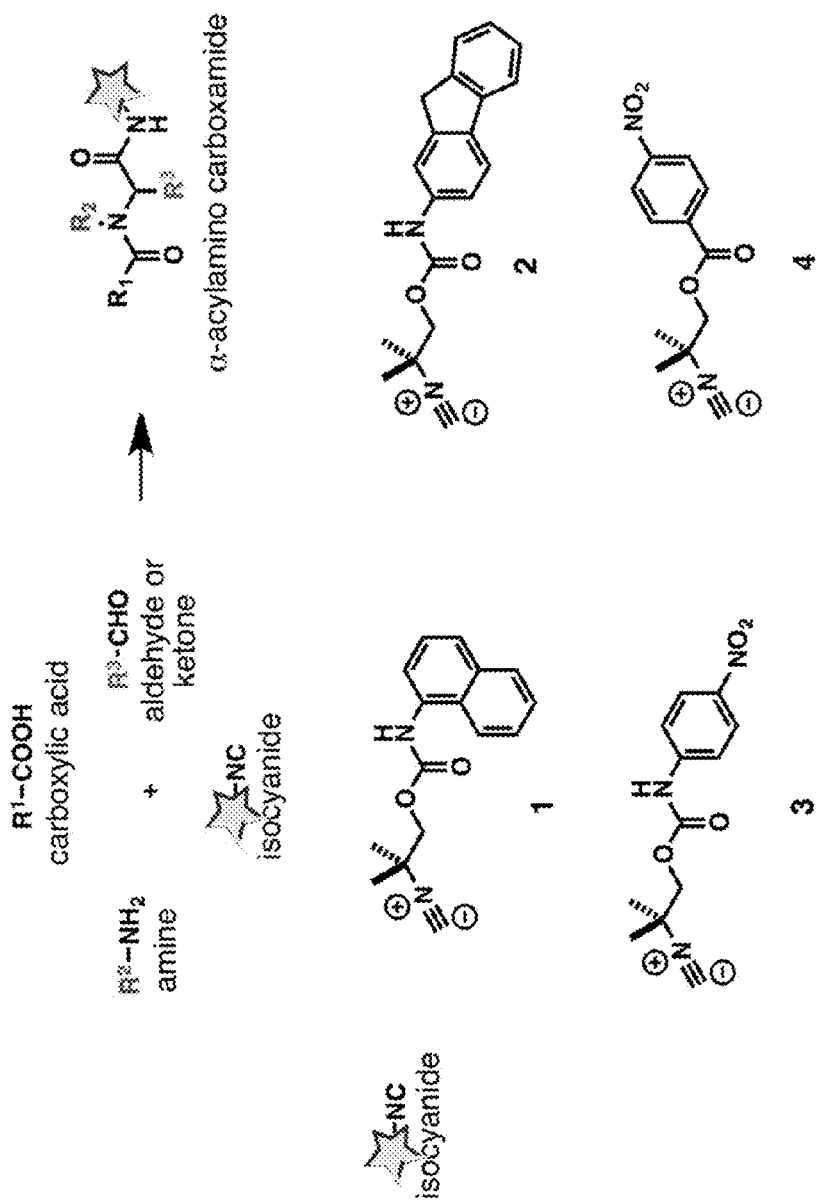
FIG. 3 depicts a prior art Ugi four-component reaction with UV-active/fluorescent isocyanides.

In an embodiment of the invention, the detection of metabolites in LC-MS is greatly facilitated if the derivatization reaction utilizes a chromophoric, isotopic or ionic substrate with an absorbance that is distinct from most metabolites. In addition to facilitating detection, the chromophore, for example, enables the relative and absolute quantifications of derivatized metabolites to be determined spectrophotometrically. Generally, commercially available LC-MS instruments have UV-Vis detectors, which can detect U-4CR reactants having chromophores. As described herein, a UV-active isocyanide for the derivatization with an isocyano functional group is rarely observed in nature. The isocyanide can be used in Ugi reactions to derivatize metabolites containing either an amine, carboxylic acid, aldehyde or ketone moiety (FIG. 3). Chromophoric isocyanides can be prepared by the reaction of ring-opened oxazolines with UV-active acyl chlorides or isocyanates. Of the four different UV-active isocyanides Scheme 2, the p-nitrophenyl-carbamoyl isocyanide is the most preferred for metabolite derivatization because it can be prepared in high yield and has a $\lambda_{max}$=320 nm, which is distinct from that of most metabolites, thereby enabling an enhancement of the signal-to-noise ratio. UV-active isocyanides do not have the typical noxious odor of isocyanides, and, as a solid, is stable in a laboratory for weeks at room temperature.

Scheme 2. The Synthesis of UV-active Isocyanides.

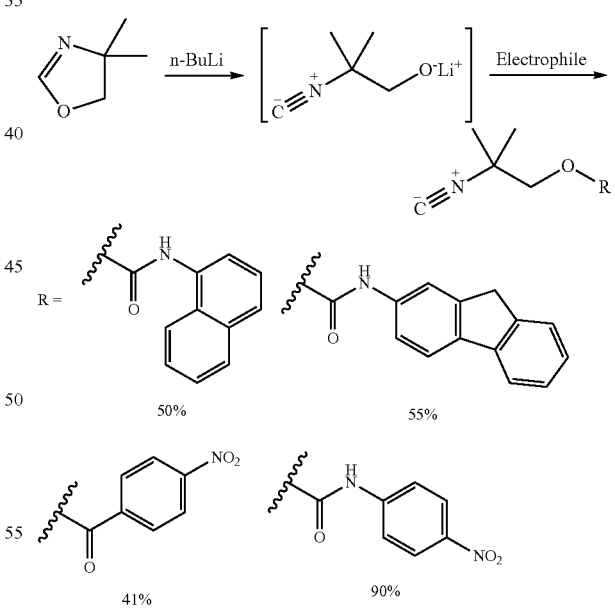

A series of reactions in which the p-nitrophenyl-carbamoyl isocyanide and isobutyraldehyde were reacted with proteinogenic α-amino acids in methanol at room temperature was performed (Scheme 3 and Table 1). Ugi and co-workers previously reported analogous reactions of α-amino acids with isocyanides and aldehydes in methanol at −30° C. (Ugi, I., et al., *Tetrahedron* 52:11657-11664 (1996)). This variant of the canonical Ugi reaction is called a "4-component 5-center"

reaction because of the bifunctional α-amino acid substrate and the participation of the methanol solvent as a reactant (Scheme 3). Despite our use of different reaction conditions and isocyanide substrates, the products observed herein were equivalent to those reported by Ugi (Ugi, I., et al., *Tetrahedron* 52:11657-11664 (1996)), except in the reactions with histidine and glutamine (Scheme 4). In our reaction with histidine, the product is linear rather than cyclic as reported by Ugi (Ugi, I., et al., *Tetrahedron* 52:11657-11664 (1996)). In the reaction reported by Ugi, the carbonyl of the isocyanoacetate substrate acts as a hydrogen bond acceptor that induces a conformer of the initial product that favors cyclization. In contrast, the isocyanide substrate in the reaction described herein with histidine lacks an appropriately oriented hydrogen bond acceptor for cyclization. In the reaction described herein with glutamine, observation of a piperidinedione structure is indicative of a ring-closure involving the amino acid's primary amide side chain. In any case, the yields and retention times of the products are reported in Table 1. Most amino acids reacted with moderate yields, with the exception of arginine and cysteine. All of the derivatized α-amino acids had unique retention times under a single chromatographic method, which is not the case for those that are not derivatized.

Scheme 3. Derivatization of Amino Acids.

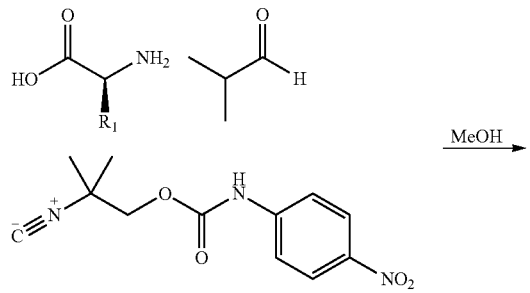

-continued

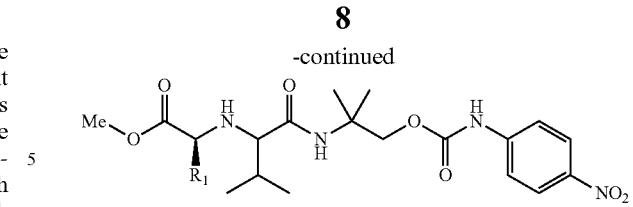

TABLE 1

Isolated Yields of Amino Acid Derivatization and Retention Times.

| Amino Acid | Yield (%) | RT (min) |
|---|---|---|
| Alanine | 59 | 4.9 |
| Arginine | N/A | N/A |
| Asparagine | 31 | 5.6 |
| Aspartate[a] | 68 | 13.3, 13.5 |
| Cysteine | N/A | N/A |
| Glutamate[a] | 70 | 13.0, 13.2 |
| Glutamine[b] | 87 | 4.8 |
| Glycine | 39 | 4.5 |
| Histidine | 96 | 4.6 |
| Isoleucine | 71 | 13.7 |
| Leucine | 68 | 9.4 |
| Lysine[c] | 69 | 4.5 |
| Methionine | 54 | 8.9 |
| Phenylalanine | 60 | 11.8 |
| Proline | 52 | 6.1 |
| Serine | 37 | 5.3 |
| Threonine | 44 | 7.3 |
| Tryptophan | 44 | 9.9 |
| Tyrosine | 72 | 8.3 |
| Valine | 76 | 10.7 |

Reactions were performed at room temperature for 2 d. Chromatographic conditions: 2.5 × 100 mm C18 reverse-phase column with a linear gradient of 30%-90% acetonitrile/0.1% formic acid in water over 16 min with UV-detection at 320 nm. In most cases, these chromatographic conditions did not enable separation of the product diastereomers.
[a]Yields refer to isolated tandem Ugi-Passerini product and the retention times reflect diastereomers.
[b]Yield refers to isolated piperidinedione product.
[c]Yield refers to isolated ε-lactam product.

Scheme 4. Unexpected Products of Glutamine and Histidine Derivatization.

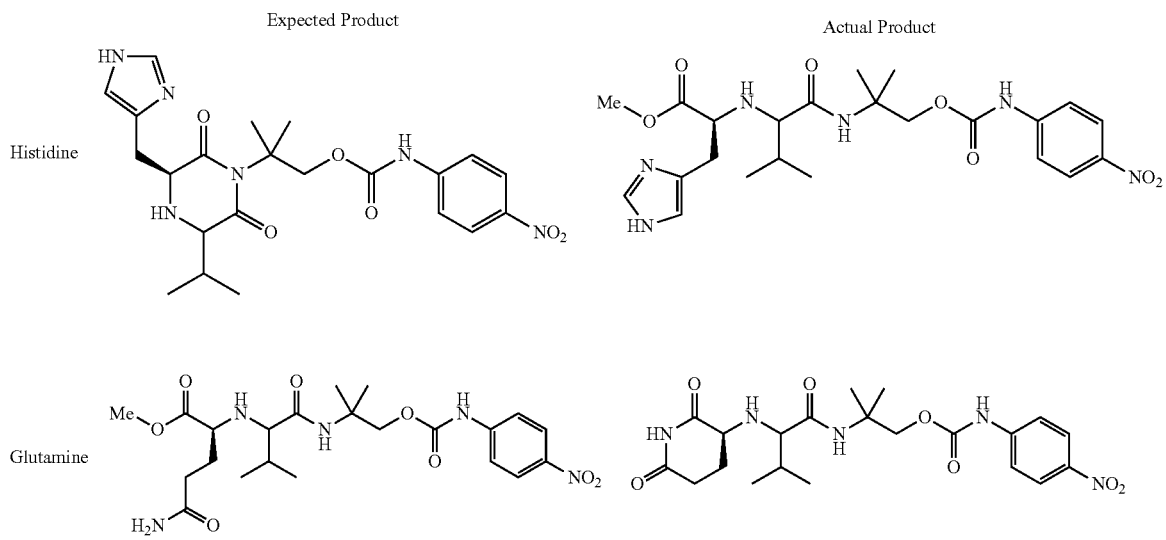

The products reported by Ugi are in the left column and the products shown in the right.

While the α-amino acid derivatizations required methanol as a substrate, it was determined whether the reactions could tolerate water. Ugi reactions are reported to be enhanced in aqueous conditions, but the yield of a model reaction with serine is significantly lower when the ratio of methanol-to-water exceeded 3:1. Water tolerance of this reaction is advantageous in the context of processing biological samples.

Given the success with α-amino acids, derivatization of a wide range of structurally and functionally diverse metabolites containing carboxylic acid, amine, aldehyde, or ketone functional groups was explored. In these reactions, analytes with the functional group of interest are reacted with p-nitrophenyl-carbamoyl isocyanide and the two other requisite substrates of the U-4CR. As illustrated in Scheme 5, fatty acids (1a-c), intermediates in central metabolism (2a-b), polyamines (3a-c), neurotransmitters (4a-d), co-enzymes (5), and hormones (6a-h) are derivatized. In most cases, good yields in these reactions are observed, regardless of the structural complexity of the metabolite. Reactions with ketone-containing metabolites have lower yields. Given the complexity of the metabolite reactants, these observations provides new insights into the substrate selectivity and tolerance of the U-4CR. For example, an exclusive reaction at the unconjugated ketone carbonyl of steroid hormones and not their conjugated ketone is observed. Further, U-4CR derivatizations of molecules with phenols do not undergo competing Ugi-Smiles reactions in which an isocyanide, aldehyde, amine and phenol react with one another.

Scheme 5.
Metabolites and Isolated Yields of Derivatization Reactions

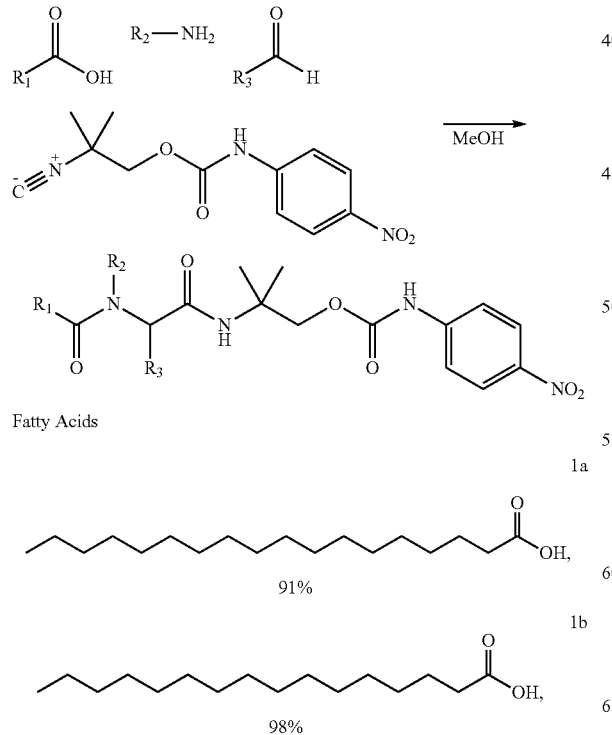

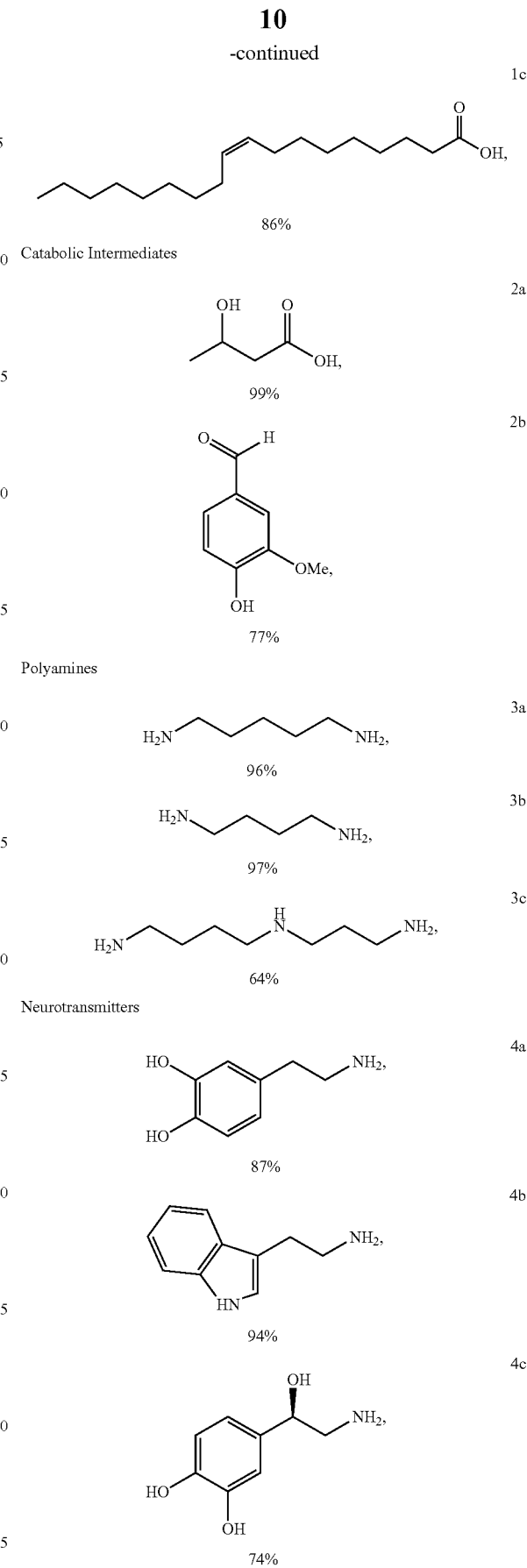

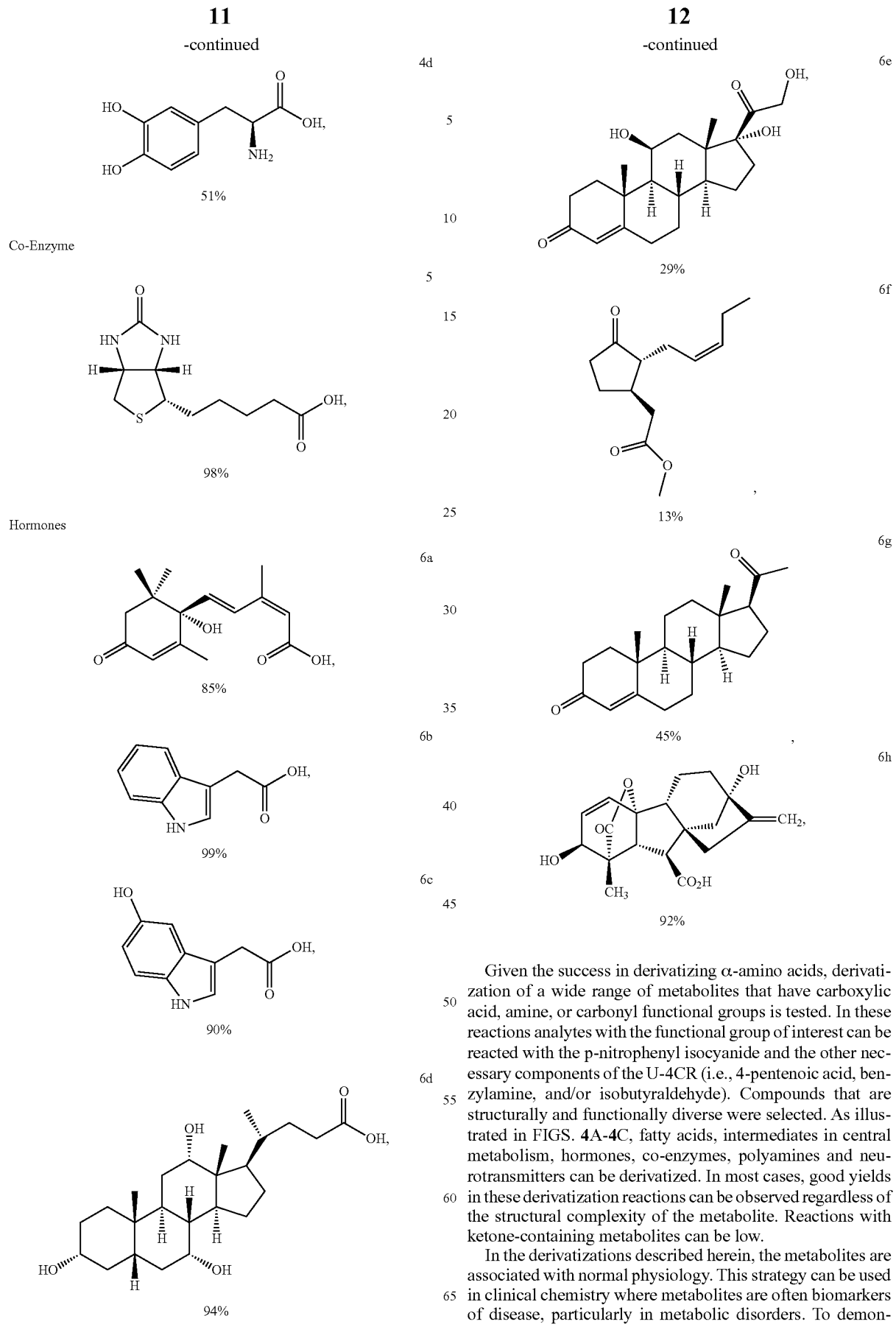

Figure 4A:
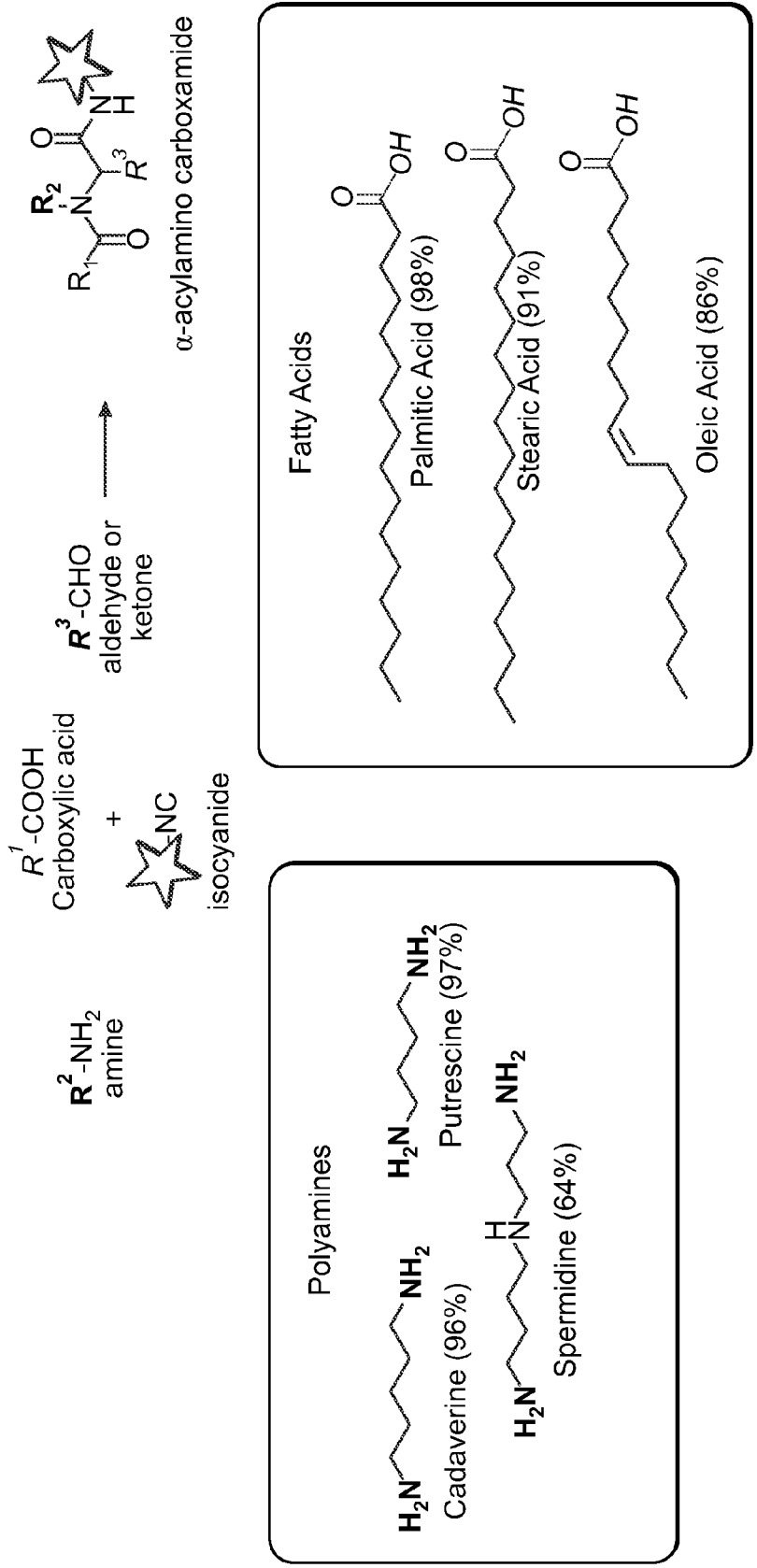
FIGS. 4A-4C depict the derivation of structurally and functionally diverse metabolites by a prior art Ugi four-component reaction.
Figure 4B:
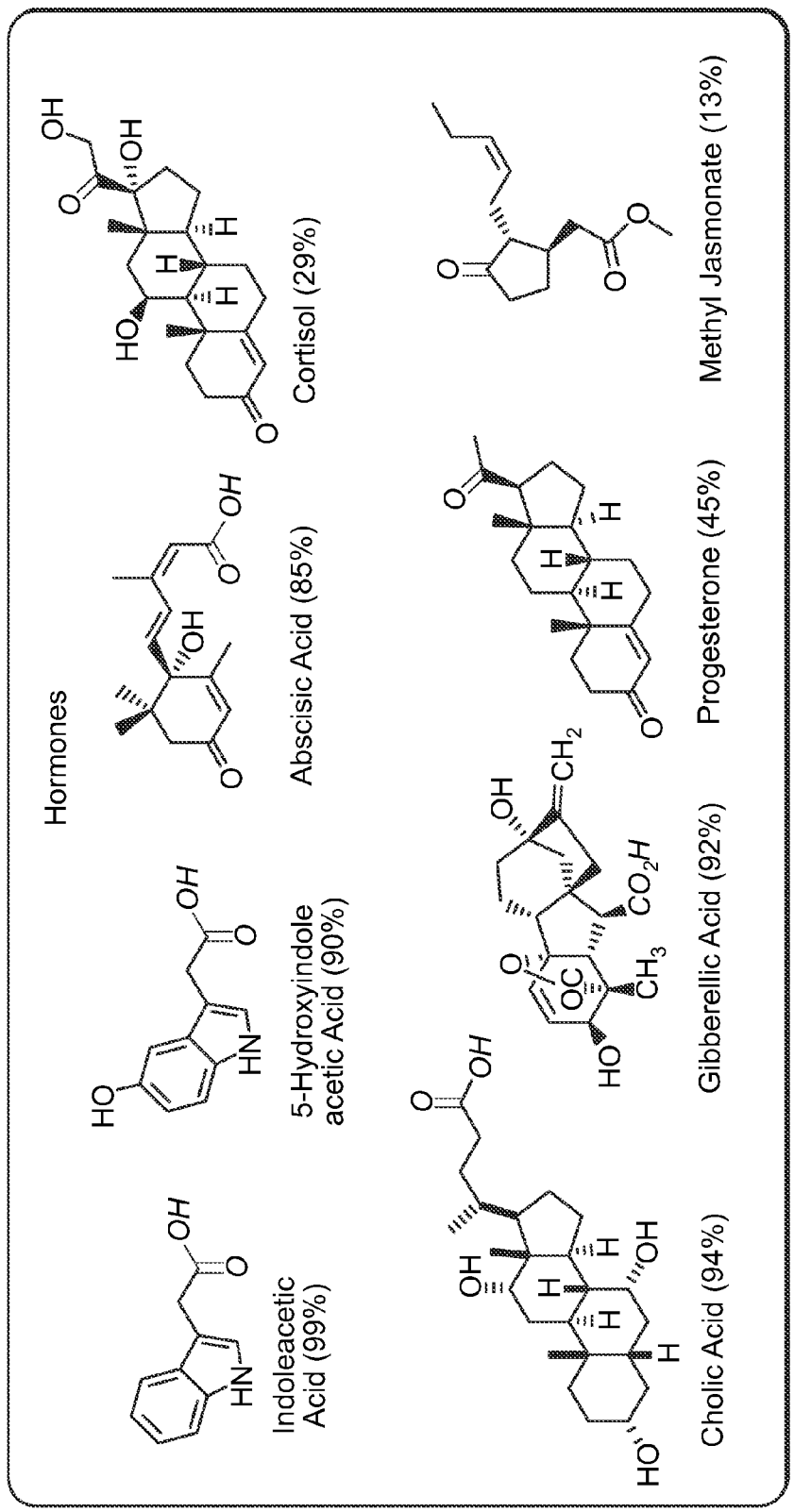
Figure 4C:
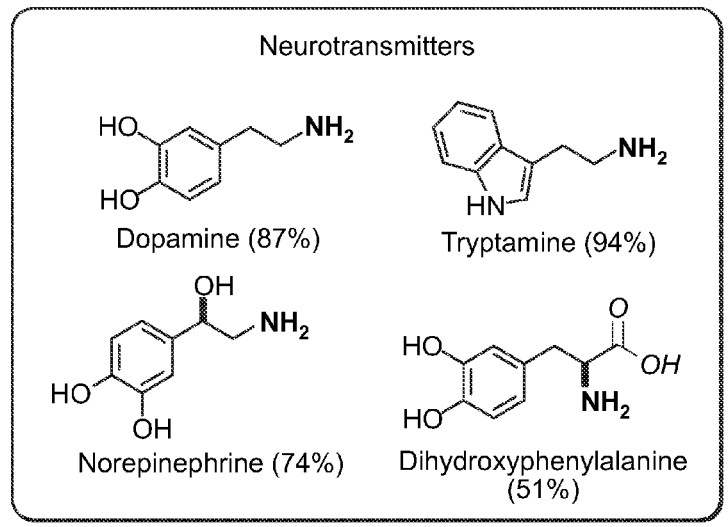
Figure 4C:
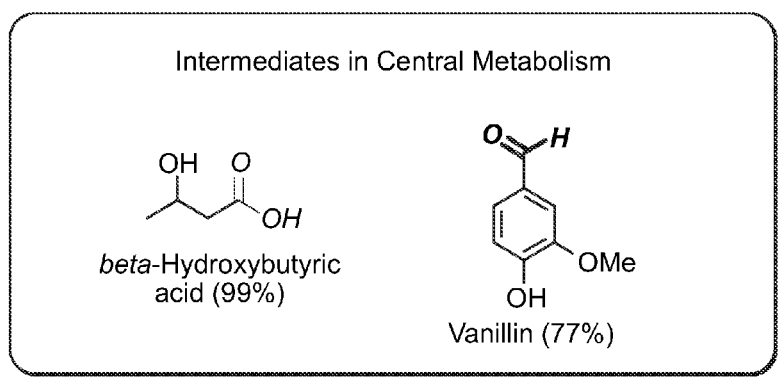
Figure 4C:
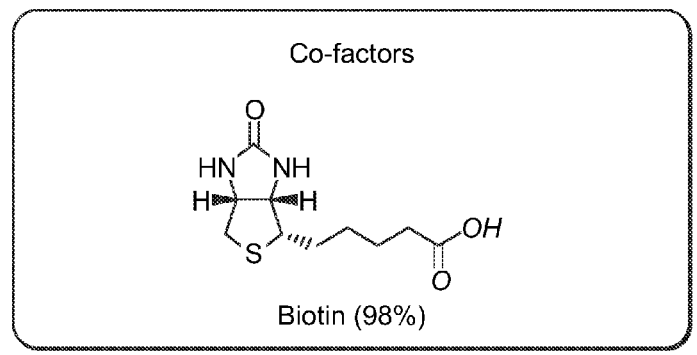

Given the success in derivatizing α-amino acids, derivatization of a wide range of metabolites that have carboxylic acid, amine, or carbonyl functional groups is tested. In these reactions analytes with the functional group of interest can be reacted with the p-nitrophenyl isocyanide and the other necessary components of the U-4CR (i.e., 4-pentenoic acid, benzylamine, and/or isobutyraldehyde). Compounds that are structurally and functionally diverse were selected. As illustrated in FIGS. 4A-4C, fatty acids, intermediates in central metabolism, hormones, co-enzymes, polyamines and neurotransmitters can be derivatized. In most cases, good yields in these derivatization reactions can be observed regardless of the structural complexity of the metabolite. Reactions with ketone-containing metabolites can be low.

In the derivatizations described herein, the metabolites are associated with normal physiology. This strategy can be used in clinical chemistry where metabolites are often biomarkers of disease, particularly in metabolic disorders. To demonstrate that this chemistry is compatible with metabolites associated with disease, reactions can be performed with biomarkers of phenylketonuria (PKU). This metabolic disorder results from a deficiency in phenylalanine hydroxylase, the enzyme that catalyzes conversion of phenylalanine into tyrosine. Individuals with PKU have excess phenylalanine in the blood and phenylalanine catabolites in their urine (i.e., phenethylamine, phenylpyruvic acid, phenyllactic acid, and phenylacetic acid). Currently, there is no reliable urine-based method for diagnosis of PKU due to difficulties in detection of these metabolites. Derivatized metabolites using the U-4CR (Table 2) are described. In the LC-MS analysis, all of the derivatized metabolites could be detected at 320 nm and exhibited closely related, but distinct retention times. Further, all of the derivatized metabolites were readily detected in the positive ion mode in elctrospray ionization-mass spectrometry (ESI-MS). The singularity of ion mode in ESI-MS analysis is a significant advantage of our derivatization chemistry because the underivatized, cationic phenethylamine is best detected under positive ion mode, but the anionic carboxylate metabolites are better detected under negative ion mode. The coalescence of the products' retention times and ionization conditions that result from the derivatization is clearly advantageous with respect to analysis. These metabolites are not derivatized in an actual urine sample from a PKU patient, the ease of analysis suggests the utility of this derivatization method in biomarker detection.

TABLE 2

Diagnostic Metabolites of PKU - Isolated Yields of Derivatization and Retention Times of Products.

| PKU Metabolites | Yield (%) | RT (min) |
|---|---|---|
| Phenethylamine | 76 | 7.4 |
| Phenylpyruvic Acid | 78 | 7.7 |
| Phenyllactic Acid | 94 | 6.6 |
| Phenylacetic Acid | 90 | 7.2 |

Chromatographic conditions: 2.5 × 100 mm C18 reverse-phase column with a linear gradient of 45%-95% acetonitrile/0.1% formic acid in water over 10 min with UV-detector set to 320 nm.

In conclusion, the chemical derivatization of metabolites is an important tool in studies of metabolism. As described herein, that the U-4CR is a compelling alternative to the "one reagent-one functional group" approach that has been used for more than a half century in metabolite derivatization. Using this multicomponent reaction with commercially available or easily prepared substrates, structurally complex metabolites containing amines, carboxylic acids, aldehydes, or ketones can be chemoselectively derivatized at room temperature under a single set of reaction conditions, even in the presence of water. Through the use of a specially designed UV-active isocyanide, the U-4CR yields products that can easily be detected, separated, and ionized under defined conditions, irrespective of metabolite structure. The methods described herein may be useful in a metabolomic analyses and disease diagnosis.

In reactions of aspartic acid and glutamic acid, the α-amino acid moieties participate in a Ugi 4-component 5-center reaction, while the carboxylate side chain participated in a Passerini reaction. This is a so-called tandem Ugi-Passerini reaction. Except for reactions with tryptophan, tyrosine and serine, our yields are higher than those reported by Ugi. In the aforementioned cases, Ugi included triethylamine presumably to enhance the nucleophilicity of methanol. These findings imply that these reactions need not be performed at −30° C. Arginine's basic guanidinium group facilitates solvolytic cleavage of the isocyanide carbamate, yielding a methyl carbamate. The poor solubility of cysteine in methanol and acetonitrile precludes efficient reaction. Benzylamine, 4-pentenoic acid, and/or isobutyraldehyde were selected for use as the other U-4CR substrates in these derivatization experiments.

W. B. Dunn, D. I. Ellis, TrAC, Trends Anal. Chem. 2005, 24, 285-294; W. Lu, B. D. Bennett, J. D. Rabinowitz, J. Chromatogr., B 2008, 871, 236-242; N. Vinayavekhin, E. A. Homan, A. Saghatelian, ACS Chem. Biol. 2010, 5, 91-103; R. Madsen, T. Lundstedt, J. Trygg, Anal. Chim. Acta 2010, 659, 23-33; R. Wei, G. Li, A. B. Seymour, Anal. Chem. (Washington, D.C., U.S.) 2010, 82, 5527-5533; A. Nordström, R. Lewensohn, J. Neuroimmunol. Pharmacol. 2010, 5, 4-17; S. S. Rubakhin, E. V. Romanova, P. Nemes, J. V. Sweedler, Nat. Methods 2011, 8, S20-S29.

B. D. Bennett, E. H. Kimball, M. Gao, R. Osterhout, S. J. Van Dien, J. D. Rabinowitz, Nat. Chem. Biol. 2009, 5, 593-599.

J. M. Halket, D. Waterman, A. M. Przyborowska, R. K. P. Patel, P. D. Fraser, P. M. Bramley, J. Exp. Bot. 2005, 56, 219-243.

G. Lunn, L. C. Hellwig, Handbook of derivatization reactions for HPLC; Wiley: New York, 1998.

E. E. Carlson, B. F. Cravatt, Nat. Methods 2007, 4, 429-435.

a) A. Dömling, I. Ugi, Angew. Chem. 2000, 39, 3168-3210; b) A. Dömling, Chem. Rev (Washington, D.C., U.S.) 2006, 106, 17-89.

I. Ugi, A. Demharter, W. Hörl, T. Schmid, Tetrahedron 1996, 52, 11657-11664.

T. Ziegler, S. Gerling, M. Lang, Angew. Chem., Int. Ed. 2000, 39, 2109-2112.

M. C. Pirrung, K. D. Sarma, J. Am. Chem. Soc. 2004, 126, 444-445.

P. J. Scheuer, Acc. Chem. Res. 1992, 25, 433-439.

T. Lindhorst, H. Bock, I. Ugi, Tetrahedron 1999, 55, 7411-7420.

S. T. M. Simila, S. F. Martin, Tetrahedron Lett. 2008, 49, 4501-4504.

L. El Kaim, M. Gizolme, L. Grimaud, J. Oble, Org. Lett. 2006, 8, 4019-4021.

K. Michals, R. Matalon, Am. J. Clin. Nutr. 1985, 42, 361-365.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of characterizing metabolites in a biological sample, comprising the steps of:
   a) combining at least a portion of a biological sample, the biological sample including at least one metabolite that is, or includes,
      i) an amino acid or an amine,
      ii) an aldehyde or a ketone, or
      iii) a carboxylic acid or an alcohol,
      with an ultraviolet-active isocyanide and Ugi reactants that consist essentially of two of i), ii) and iii) apart from the metabolite, thereby derivatizing at least a portion of that metabolite; and
   b) characterizing the derivatized metabolite of the biological sample.

2. The method of claim 1, wherein the metabolite is a first metabolite, and wherein the biological sample includes a second metabolite that is, or includes,
   i) an amino acid or an amine,
   ii) an aldehyde or a ketone, or
   iii) a carboxylic acid or an alcohol,
   that is not any of i), ii) or iii) of the first metabolite, and further including the steps of
   a) combining at least a portion of the biological sample with an ultraviolet-active isocyanide and Ugi reactants that consist essentially of two of i), ii) and iii) apart from the second metabolite, thereby derivatizing at least a portion of the second metabolite; and
   b) characterizing the derivatized second metabolite.

3. The method of claim 1, wherein the metabolite is selected from the group consisting of polyamines, fatty acids, neurotransmitters, hormones, α-amino acids, intermediates in central metabolism, and co-enzymes.

4. The method of claim 1, wherein the metabolite includes an amine.

5. The method of claim 1, wherein the metabolite includes an aldehyde.

6. The method of claim 1, wherein the metabolite includes a ketone.

7. The method of claim 1, wherein the metabolite includes a carboxylic acid.

8. The method of claim 1, wherein the metabolite includes an α-amino acid.

9. The method of claim 1, wherein the biological sample includes a plurality of chemically distinct metabolites sharing a common functional group of,
   i) an amino acid or an amine,
   ii) an aldehyde or a ketone, or
   iii) a carboxylic acid or an alcohol.

10. The method of claim 9, wherein the step of characterizing the derivatized metabolites includes separating at least a portion of the derivatized metabolites from each other.

11. The method of claim 10, wherein the derivatized metabolites are separated from each other by liquid chromatography.

12. The method of claim 11, wherein the derivatized metabolites are characterized, at least in part, by mass spectroscopy.

* * * * *